United States Patent
Garcia Duran et al.

(10) Patent No.: US 11,301,774 B2
(45) Date of Patent: Apr. 12, 2022

(54) SYSTEM AND METHOD FOR MULTI-MODAL GRAPH-BASED PERSONALIZATION

(71) Applicant: NEC Europe Ltd., Heidelberg (DE)

(72) Inventors: Alberto Garcia Duran, Heidelberg (DE); Mathias Niepert, Heidelberg (DE)

(73) Assignee: NEC CORPORATION, Tokyo (JP)

(*) Notice: Subject to any disclaimer, the term of this patent is extended or adjusted under 35 U.S.C. 154(b) by 1350 days.

(21) Appl. No.: 15/593,353

(22) Filed: May 12, 2017

(65) Prior Publication Data

US 2018/0247224 A1     Aug. 30, 2018

Related U.S. Application Data

(60) Provisional application No. 62/464,497, filed on Feb. 28, 2017.

(51) Int. Cl.
    *G06N 20/00*      (2019.01)
    *G06N 5/04*      (2006.01)
    (Continued)

(52) U.S. Cl.
    CPC ............ *G06N 20/00* (2019.01); *G06N 5/022* (2013.01); *G06N 5/04* (2013.01); *G16H 50/20* (2018.01);
    (Continued)

(58) Field of Classification Search
    CPC ........ G06N 5/04; G06N 20/00; G06N 99/005; G08B 27/001; G08B 21/02; G08B 5/36; G06F 19/345; G16H 50/20; G16H 50/70
    See application file for complete search history.

(56) References Cited

U.S. PATENT DOCUMENTS 7,320,031 B2    1/2008   Konig et al.
8,341,745 B1*   12/2012   Chau ...................... G06F 21/56
                                                                    726/24
(Continued)

OTHER PUBLICATIONS

Liu, J. (2010). Privacy Preserving in Serial Data and Social Network Publishing (Doctoral dissertation, Chinese University of Hong Kong). (Year: 2010).*

(Continued)

*Primary Examiner* — Michael J Huntley
*Assistant Examiner* — Oluwatosin O Alabi
(74) *Attorney, Agent, or Firm* — Leydig, Voit & Mayer, Ltd.

(57) ABSTRACT

A method for learning latent representations of individual users in a personalization system uses a graph-based machine learning framework. A graph representation is generated based on input data in which the individual users are each represented by a node. The nodes are associated with labels. Node vector representations are learned by combining label latent representations from a vertex and neighboring nodes so as to reconstruct the label latent representation of the vertex and updating the label latent representations of the neighboring nodes using gradients resulting from application of a reconstruction loss. A classifier/regressor is trained using the node vector representations and the node vector representations are mapped to personalizations. Actions associated with the personalizations are then initiated.

17 Claims, 7 Drawing Sheets
(4 of 7 Drawing Sheet(s) Filed in Color)

(51) Int. Cl.
- *G06N 5/02* (2006.01)
- *G16H 50/20* (2018.01)
- *G16H 50/70* (2018.01)
- G08B 27/00 (2006.01)
- G08B 21/02 (2006.01)
- G08B 5/36 (2006.01)

(52) U.S. Cl.
CPC ............... *G16H 50/70* (2018.01); *G08B 5/36* (2013.01); *G08B 21/02* (2013.01); *G08B 27/001* (2013.01)

(56) References Cited

U.S. PATENT DOCUMENTS

| | | | |
|---|---|---|---|
| 8,538,169 | B2 | 9/2013 | Hido |
| 8,781,915 | B2* | 7/2014 | Herrich ............ G06Q 30/0633 705/26.7 |
| 9,082,082 | B2* | 7/2015 | Jebara .................... G06Q 50/00 |
| 9,384,571 | B1 | 7/2016 | Covell et al. |
| 2013/0024464 | A1* | 1/2013 | Berner .................. G06F 16/951 707/749 |
| 2013/0041876 | A1 | 2/2013 | Dow et al. |
| 2013/0231953 | A1* | 9/2013 | Ebadollahi ............ G06Q 50/22 705/3 |
| 2014/0244293 | A1 | 8/2014 | Jones, III |
| 2016/0379128 | A1* | 12/2016 | Bouchard .............. G06N 20/00 706/12 |
| 2017/0124400 | A1* | 5/2017 | Yehezkel Rohekar .. G06K 9/52 |
| 2018/0082172 | A1* | 3/2018 | Patel .................... G06N 3/0472 |

OTHER PUBLICATIONS

Zheng, Q., & Skillicorn, D. B. (May 2015,). Analysis of criminal social networks with typed and directed edges. In 2015 IEEE International Conference on Intelligence and Security Informatics (ISI) (pp. 1-6). IEEE. (Year: 2015).*

Fischer, I. (2005). Graph Transformations and Neural Networks. In Encyclopedia of Data Warehousing and Mining (pp. 534-539). IGI Global. (Year: 2005).*

Wei, C., Luo, S., Ma, X., Ren, H., Zhang, J., & Pan, L. (2016). Locally embedding autoencoders: a semi-supervised manifold learning approach of document representation. PloS one, 11(1), e0146672. (Year: 2016).*

Xiang, W. (2012). Transfer learning with open web data (Doctoral dissertation, Hong Kong University of Science and Technology). (Year: 2012).*

Gilmer, J., Schoenholz, S. S., Riley, P. F., Vinyals, O., & Dahl, G. E. (Jul. 2017,). Neural message passing for quantum chemistry. In International Conference on Machine Learning (pp. 1263-1272). PMLR. (Year: 2017).*

Choi, B. S., & Van Meter, R. (2011). On the effect of quantum interaction distance on quantum addition circuits. ACM Journal on Emerging Technologies in Computing Systems (JETC), 7(3), 1-17. (Year: 2011).*

Dai, H., Dai, B., & Song, L. (Jun. 2016,). Discriminative embeddings of latent variable models for structured data. In International conference on machine learning (pp. 2702-2711). PMLR. (Year: 2016).*

Grover, A., & Leskovec, J. (Aug. 2016,). node2vec: Scalable feature learning for networks. In Proceedings of the 22nd ACM SIGKDD international conference on Knowledge discovery and data mining (pp. 855-864). (Year: 2016).*

Jacob Y, Denoyer L, Gallinari P. Learning latent representations of nodes for classifying in heterogeneous social networks. InProceedings of the 7th ACM international conference on Web search and data mining Feb. 24, 2014 (pp. 373-382). (Year: 2014).*

Yedidia, J. S. "Message-Passing Algorithms for Optimization and Inference: Belief Propagation and Divide &Concur." (2011). (Year: 2011).*

Bryan Perozzi, et al., "DeepWalk: online learning of social representations", Proceeding KDD '14 Proceedings of the 20th ACM SIGKDD international conference on Knowledge discovery and data mining, pp. 701-710, Aug. 24-27, 2014.

Andrea Frame, et al., "DeViSE: A Deep Visual-Semantic Embedding Model", Advances in Neural Information Processing Systems 26 (NIPS 2013), pp. 1-11, Dec. 10-10, 2013.

Alex Krizhevsky, et al., "ImageNet Classification with Deep Convolutional Neural Networks", Advances in Neural Information Processing Systems 25 (NIPS 2012), Dec. 3-8, 2012.

Tomas Mikolov, et al., "Distributed Representations of Words and Phrases and their Compositionality", Advances in Neural Information Processing Systems 26 (NIPS 2013), pp. 1-9, Oct. 2013.

Sofus A. Macskassy, et al., "A Simple Relational Classifier", New York University NY Stern School of Business, pp. 1-13, Dec. 2003.

Zhilin Yang, et al., "Revisiting Semi-supervised learning with graph embeddings", Proceeding ICML '16 Proceedings of the 33rd International Conference on International Conference on Machine Learning—vol. 48, pp. 1-9, Jun. 19-24, 2016.

* cited by examiner

SYSTEM AND METHOD FOR MULTI-MODAL GRAPH-BASED PERSONALIZATION

CROSS-REFERENCE TO PRIOR APPLICATIONS

Priority is claimed to U.S. Provisional Patent Application No. 62/464,497, filed on Feb. 28, 2017, the entire disclosure of which is hereby incorporated by reference herein.

FIELD

The present invention relates to a personalization system and a method for learning latent representations of individual users in a personalization system using a graph-based machine learning framework.

BACKGROUND

In numerous applications, the guiding objective is to turn behavioral patterns and attributes of users into a personalization, that is, a service, product, or treatment that fits the user's interest or reflects the user's intentions. Examples are online advertisements where the users' behavior and attributes are mapped to a product category or even individual products that the user might be interested to purchase. In personalized medicine, the objective is to map patients (based on lab results, imaging results, patient record data, history of diseases, etc.) into a treatment plan that fits the patient's personal traits and symptoms.

Graph-structured data occurs in numerous application domains such as social networks, bioinformatics, natural language processing and relational knowledge bases. The computational problems commonly addressed in these domains are network classification, statistical relational learning, link prediction, and anomaly detection, among others. In addition, graph-based methods for unsupervised and semi-supervised learning are often applied to data sets with few labeled examples. For instance, spectral decompositions and locally linear embeddings (LLE) are always computed for a data set's affinity graph, that is, a graph that is first constructed using domain knowledge or some measure of similarity between data points.

There are numerous methods for embedding learning such as multidimensional scaling (MDS), Laplacian Eigenmap, Siamese networks, IsoMap, and LLE. Most of these approaches construct an affinity graph on the data points first and then embed the graph into a low dimensional space. The corresponding optimization problems often have to be solved in closed form (for instance, due to constraints on the objective that remove degenerate solutions) which is intractable for large graphs.

Graph neural networks (GNN) is a general recursive neural network for graphs where each node is associated with one label. Learning is performed with the Almeida-Pineda algorithm. The computation of the node embeddings is performed by back-propagating gradients for a supervised loss after running a recursive propagation model to convergence. This is both time and memory consuming.

DEEPWALK applies a word embedding algorithm to random walks. The idea is that random walks (node sequences) are treated as sentences (word sequences). A SKIPGRAM model is then used to learn node embeddings from the random walks. NODE2VEC is identical to DEEPWALK with the exception that it explores new methods to generate random walks (the input sentences to WORD2VEC), at the cost of introducing more hyperparameters. LINE optimizes similarities between pairs of node embeddings so as to preserve their first and second-order proximity. The main advantage of GEMP over these approaches is its ability to incorporate graph attributes such as text and continuous features. PLANETOID combines a learning objective similar to that of DEEPWALK with supervised objectives. It also incorporates bag of words associated with nodes into these supervised objectives.

SUMMARY

In an embodiment, the present invention provides a method for learning latent representations of individual users in a personalization system using a graph-based machine learning framework. A graph representation is generated based on input data in which the individual users are each represented by a node. The nodes are associated with labels. Node vector representations are learned using message passing. A classifier/regressor is trained using the node vector representations and mapping the node vector representations are mapped to personalizations. Actions associated with the personalizations are then initiated. Particular applications include digital health, public safety and online advertisements.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The present invention will be described in even greater detail below based on the exemplary figures. The invention is not limited to the exemplary embodiments. All features described and/or illustrated herein can be used alone or combined in different combinations in embodiments of the invention. The features and advantages of various embodiments of the present invention will become apparent by reading the following detailed description with reference to the attached drawings which illustrate the following.

DETAILED DESCRIPTION

Embodiments of the present invention use what is referred to herein as Graph Embeddings via Message Passing (GEMP), an unsupervised learning framework for graph-structured data. GEMP learns vector representations of graphs by passing two types of messages between neighboring nodes. Forward messages consist of label representations such as representations of words and other features associated with the nodes. Backward messages consist of the gradients that result from aggregating the representations and applying a reconstruction loss. Node representations are finally computed from the representation of their labels. Despite requiring significantly fewer parameters and hyperparameters, an instance of GEMP is competitive with and often outperforms state of the art unsupervised learning methods on a range of benchmark data sets.

GEMP learns vector representations (embeddings) of graphs by passing messages between neighboring nodes. Whenever a computational process can be mapped to message exchanges between nodes, it is implementable in graph processing frameworks such as PREGEL, GRAPHLAB and GRAPHX.

Graph labels represent vertex attributes such as bag of words, movie genres, categorical features, and discretizations of continuous features. In the GEMP learning framework, each vertex sends and receives two types of messages. Despite its conceptual simplicity, GEMP generalizes several existing graph-based machine learning approaches. Moreover, a simple instantiation of GEMP is competitive with and often outperforms existing learning approaches for graph-structured data. With far fewer parameters and hyperparameters, its learned embeddings outperform the state of the art on a range of vertex classification data sets. Since GEMP learns embeddings by incorporating different label types (representing, for instance, text and images) it is a framework for learning with multi-modal data.

Some major advantages of GEMP compared to the state of the art include: (i) gradients are computed and back-propagated immediately for each node (in contrast, e.g., to GNN), (ii) nodes in the graph can be associated with several labels and there are several label types, (iii) the unsupervised learning of vertex representations and (iv) an ability to incorporate graph attributes such as text and continuous features.

The input to the class of problems addressed by the proposed invention is (1) a set of users (new users can be added continuously), (2) a set of attribute values a user is associated with; and (3) the relations the user might have with other users and entities. Examples are user-specific features such as age, gender, lab results; and relations to other users and entities such as location, hospitals visited, and websites requested. The output of the class of problems is a vector representation for each user that is used in a classifier or regressor to map the user to a particular personalization.

A system and method are proposed that feature a novel machine learning framework for learning representations of individual users in a personalization system. The embodiments of the proposed method and system include particular environments in which a user-specific machine learning model is required for analytics and prediction tasks to effect improvements in particular fields of application. Examples of such particular applications are (a) personalized medicine; (b) online advertisement; and (c) public safety. In each of these possible embodiments, a user is associated with (i) her relationships with other users and/or other entities in the environment and (ii) attributes of varying types (numerical, image, text, etc.) that pertain to the individual user. For instance, in the personalized medicine embodiment, the relations model family relationships and visits to hospitals and the attributes medical imaging data and lab results. The method is a novel graph-based machine learning framework that learns vector representations for individual users which can then be used for personalization tasks such as personalized medicine, personal advertisements, and crime threat prediction.

The proposed method and system generates a graph representation based on the input data. Every node of the graph represents a user or entity (such as a doctor, a hospital, etc.). Nodes are associated with the attributes of a user. Every attribute is associated with a label type and every attribute value is associated with a label. Edges model relations between users and between users and other entities.

Figure 1:
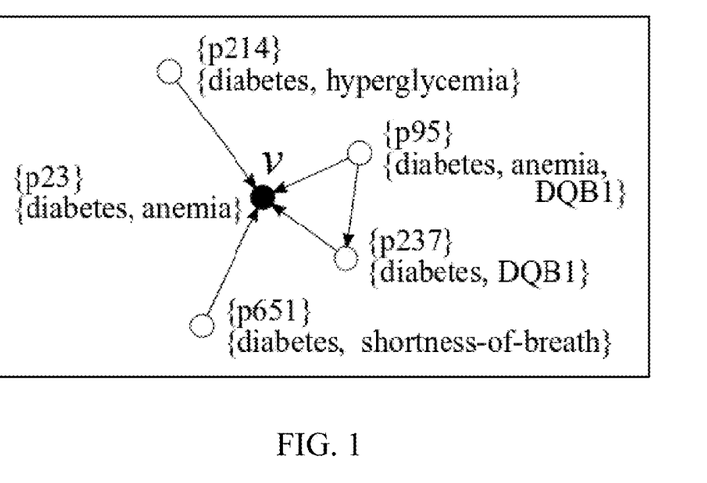
FIG. 1 shows a fragment of a graph in an embodiment of the invention for personalized medicine embodiment.

FIG. 1 depicts an example of graph representations for the personalized medicine embodiment. The nodes are patients. The first label type represents the patient identifiers. The second label type represents the positive outcome of certain medical test, lab results, and genetic markers. The proposed method, according to an embodiment, addresses the following technical problem: Given a graph representation such as the one above, learn vector representations of the nodes (here: patients) that are especially suitable for downstream personalization tasks (here: personalized medicine). The computation of the vector representations (also referred to as embeddings) has to be efficient and applicable to very large graphs. The computation of a vector representation for a new node (here: patient) has to be executable in the sub second range without having to retrain a machine learning model.

Figure 5:
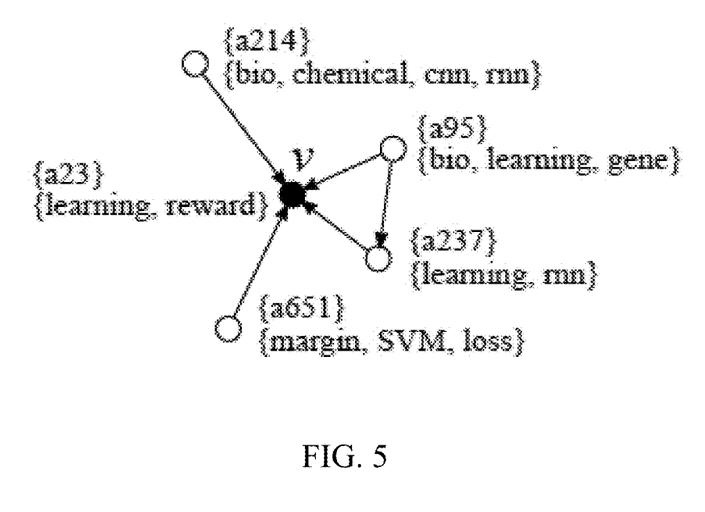
FIG. 5 shows a fragment of a graph of a citation network.

Embodiments of the proposed invention maintain a graph representation. The nodes of such graphs are associated with labels. A label is an identifier of some object and not to be confused with the notion of a class label in classification problems. Labels allow to represent a wide range of objects associated with the vertices such as words, movie genres, and discretizations of continuous features. To illustrate the concept of label types, FIG. 1 depicts a fragment of a patient-disease network. FIG. 5 depicts a fragment of a generic citation network. The first set of labels represents the article identifiers. The second set of labels represents the words mentioned in the article. Citations between articles are represented with directed edges.

According to an embodiment, the machine learning component consists of a message passing method that operates on top of the graph representation. During the training of the machine learning model each vertex v of the graph representation sends and receives two types of messages. Label representations are sent from v's neighboring nodes to v and are combined so as to reconstruct the representations of v's labels. The gradients resulting from the application of some reconstruction loss are sent back as messages to the neighboring vertices so as to update their labels' representations and the representations of v's labels. This process is repeated for a certain number of iterations or until a convergence threshold is reached. Finally, the label representations of v are used to compute a representation of v itself.

Figure 2:
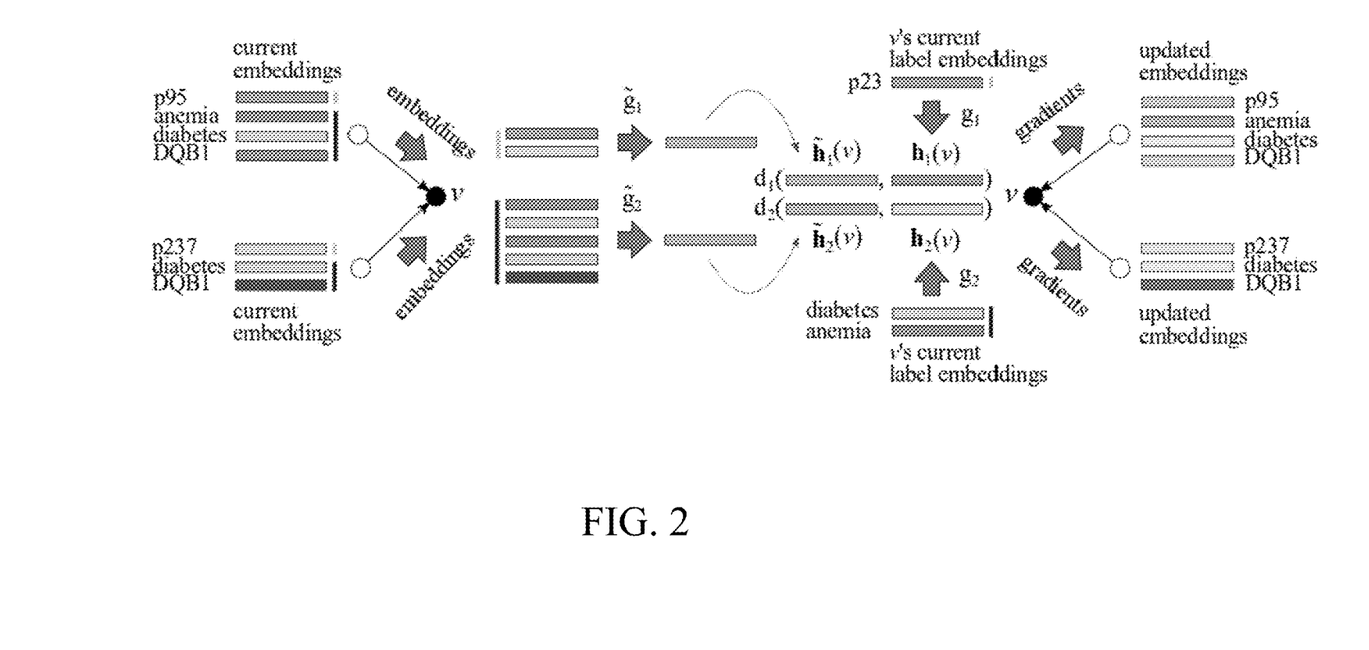
FIG. 2 shows messages passed between a vertex v and its neighbors for the graph of FIG. 1 for updating label embeddings.

FIG. 2 illustrates the messages passed between a vertex v and its neighbors for the patient-disease network of FIG. 1. First, the label embeddings are sent from the neighboring vertices to the vertex v (black node). These embeddings are fed into differentiable functions $g_i$. Here, there is one function for the article identifier label type (light gray shades) and one for the natural language words label type (dark gray shades). The gradients are derived from the distances $d_i$ between (i) the output of the functions $g_i$ applied to the embeddings sent from v's neighbors and (ii) the output of the functions $g_i$ applied to v's label embeddings. The better the output of the functions $g_i$ is able to reconstruct the output of the functions $g_i$ the smaller the value of the distance measure. The gradients are the messages that are propagated back to the neighboring nodes so as to update the corresponding embedding vectors. Gradients move the label latent representations in the Euclidean space so that eventually the reconstruction loss reaches a minimum; since, in essence, these gradients are intended to minimize the reconstruction loss.

A main purpose of the machine learning component is to learn the parameters of the functions $g_i$ and $g_i$ (if such parameters exist) and the vector representations of the labels such that the output of $g_i$ applied to the label embeddings of v's neighbors is close to the output of $g_i$ applied to the label embeddings of v. For each vertex v the messages passed to v from its neighbors are the representations of their labels. The messages passed back to v's neighbors are the gradients which are used to update the label embeddings of the neighboring nodes. FIG. 2 illustrates the first part of the unsupervised learning framework for a part of a patient-disease network. A representation is learned both for the patient identifiers and the outcome of certain medical tests carried out over the patient. The gradients are computed based on a loss function between the reconstruction of the label type embeddings and their current values.

Figure 3:
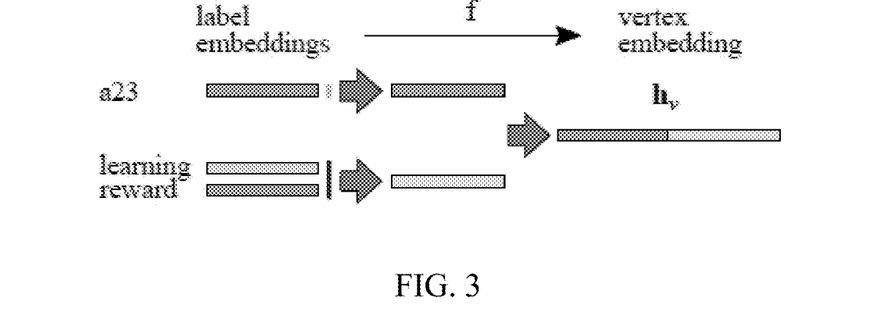
FIG. 3 shows a function for computing a vector representation of the vertex v.

The second step of the proposed learning framework applies a function f to compute the latent representations of the vertex v from the latent representations of v's labels. FIG. 3 illustrates the second step the proposed machine learning component. For each vertex v, the function f computes a vector representation of the vertex based on the vector representations of v's labels. Here, the label embeddings are first averaged for every label type and the resulting embeddings are concatenated.

One of the major advantages of the proposed machine learning component is its ability to very efficiently compute an embedding for a newly added vertex based on the embeddings of its neighboring neighbors since label latent representations are reconstructed from the representations of neighboring nodes. This implies that a node representation can be computed for a new user by, for instance, averaging the vector representations of the label types of the neighboring vertices, without the need of retraining our model. This scenario happens quite often in real-world systems, and referred to as inductive setting. Thus, one way the proposed learning component directly effects improvements in the implemented computer systems is by computing embeddings for a newly added vertex faster and utilizing less computing power and memory.

Figure 4:
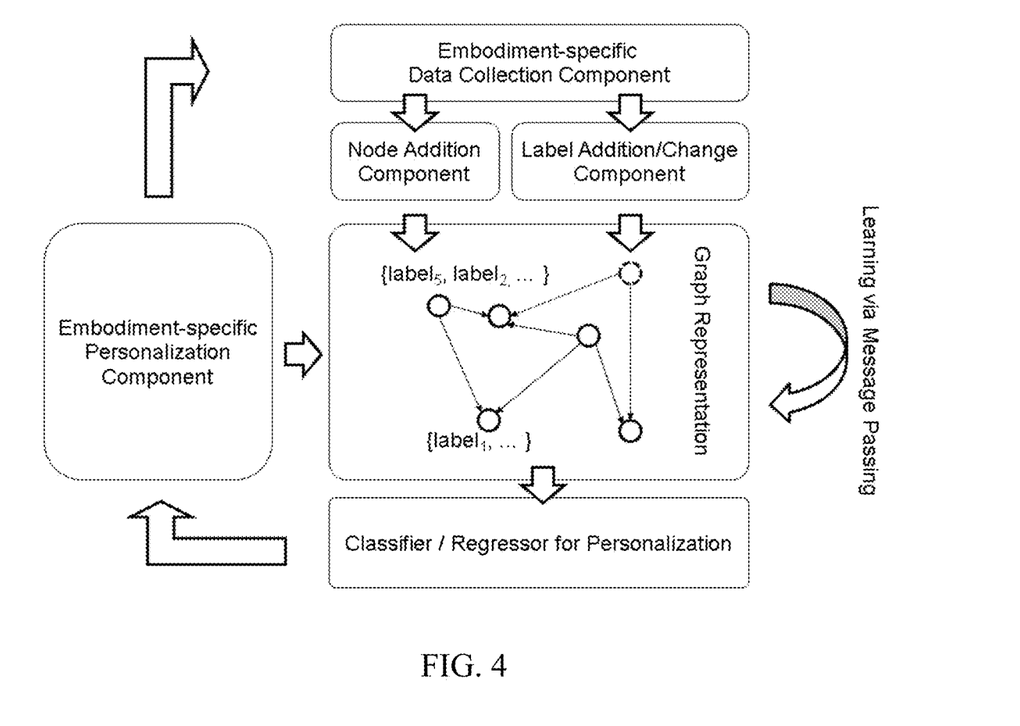
FIG. 4 is a schematic view of a personalization system having the graph representation learning component according to an embodiment of the invention.

The overall system schematically in FIG. 4 in a generic way with the overall personalization system with the graph representation learning component at the center. The Classifier/Regressor is trained on the learned vector representations so as to achieve the best performance on some personalization task (e.g., online advertisement and personalized medicine). The overall system consisting of six main components: Data Collection Component, Node Addition Component, Label Addition/Change Component, Graph Representation and Learning Component, Classifier/Regressor for Personalization Component, and Personalization Component.

The Data Collection Component is specific to the embodiment. It collects data associated to users (identified by label IDs) and passes this information to the Label Addition and Change Component.

The Node Addition Component is responsible for adding new nodes to the graph representation. For instance, in the digital health embodiment, if a new patient is added to the system, the component adds the node to the graph representation and also creates edges between the new node and existing nodes in the graph. The method for adding edges is embodiment specific.

The Label Addition/Change Component is responsible for updating the labels of the nodes in the graph representation and for changing labels if such changes occur.

The Graph Representation Component (GEMP-B) maintains the graph but also re-computes the node vector representations on a continuous basis via the massage passing approach presented before. The outputs of the component are vector representations for each of the node of the graph representation. These node representations are used to train a classifier/regressor.

The Classifier/Regressor for Personalization Component uses the vector representations maintained by the Graph Representation Component and maintains a set of classifiers/regressors that map vector representations to a set of personalization decisions. For example, the mapping from a set of symptoms to a disease, and from a disease to a treatment can be taken from medical records. Representations for the patients are learned based on their symptoms (X-ray, blood test . . . ), so standard data sets can be used to train this Component.

The Personalization Component takes the output of the Classifier/Regressor for Personalization Component and initiates the actions associated with the type of personalization. For instance, in the Online Advertisement embodiment, the component might take the product category returned by the Classifier/Regressor for Personalization Component and display an advertisement based on a bidding strategy in an online advertisement exchange system. The component also provides feedback to the Graph Representation Component (for instance, providing feedback on the quality of the personalization and the reaction of the user to the personalization).

In the following, a proposed method for embedding learning via message passing is described. A graph G=(V, E) consists of a set of vertices V and a set of edges $E \subseteq \{(v,w)|v,w \in V\}$. The approach works with directed and undirected edges and also with several edge types. N(v) is the set of neighbors of v if G is undirected and the set of in-neighbors if G is directed. The graph G s associated with a set of k label classes $L=\{L_1, \ldots, L_k\}$ where each $L_i$ is a set of labels corresponding to label type i. A label is an identifier of some object and not to be confused with the notion of a class label in classification problems. Labels allow representation of a wide range of objects associate with the vertices such as words, movie genres, and discretizations of continuous features. There are two label types: one representing the unique article identifiers and the other representing the identifiers of natural language words occurring in the articles.

The functions $l_i: V \rightarrow 2^{L_i}$ map every vertex in the graph to a subset of the labels $L_i$ of label type i. $l(v) = \cup_i l_i(v)$ represents the set of all labels associated with vertex v. $l_i(N(v)) = \{l_i(u)|u \in N(v)\}$ represents the multiset of labels of type i associated with the neighbors of vertex v.

In summary, an embodiment of the proposed machine learning component performs the following two steps 1. It learns a vector representation for every label by passing messages along the edges of the input graph, $h_l$ representing the current vector representation of a label l; and 2. It computes a vector representation for every vertex v of the input graph from the vector representations of v's labels, $h_v$ representing the current vector representation of a vertex v.

Figure 6:
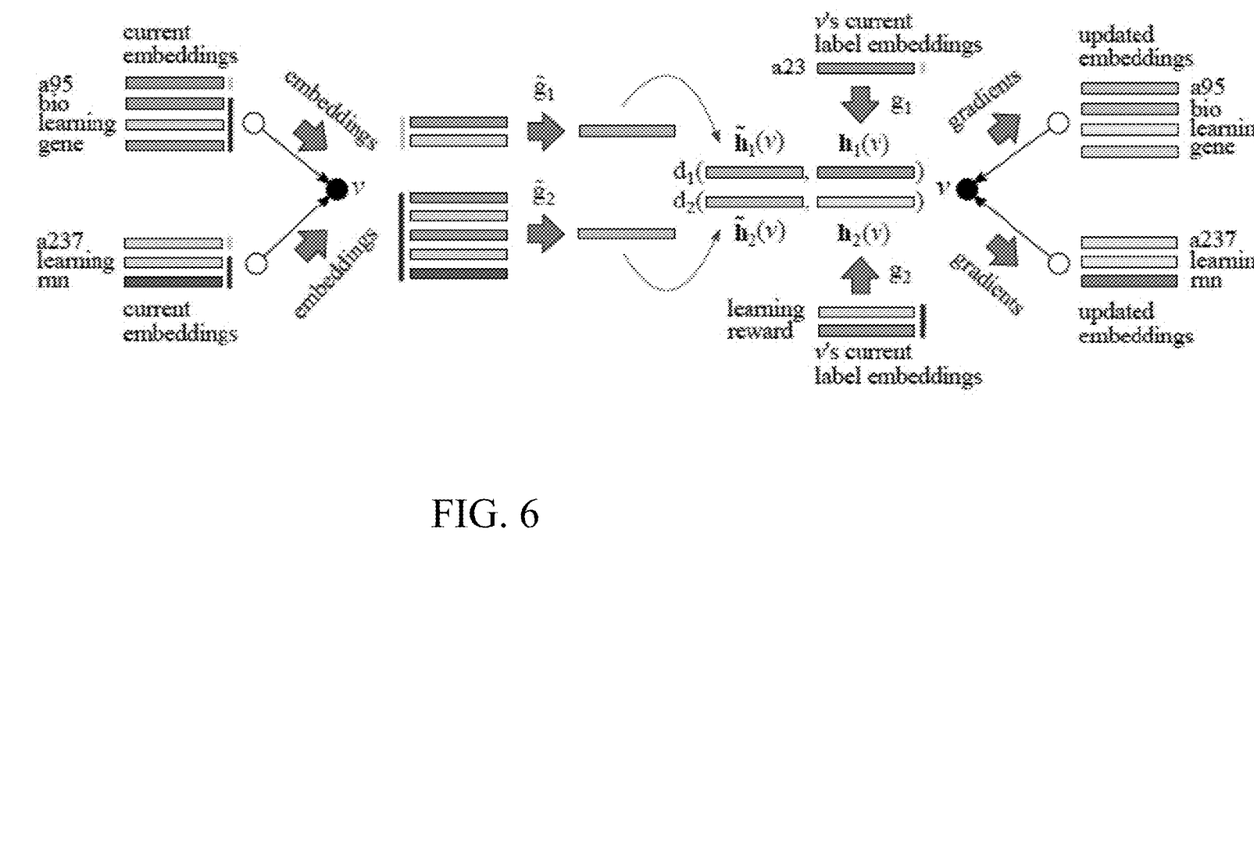
FIG. 6 shows messages passed between a vertex v and its neighbors for the graph of FIG. 5 for updating label embeddings.

FIG. 6, in a similar manner to FIG. 2, and best seen in color, illustrates the messages passed between a vertex v and its neighbors for the citation network of FIG. 5. First, the label embeddings are sent from the neighboring vertices to the vertex v (black node). These embeddings are fed into differentiable functions $\tilde{g}_i$. Here, there is one function for the article identifier label type (yellow shades) and one for the natural language words label type (red shades). The gradients are derived from the distances $d_i$ between (i) the output of the functions $\tilde{g}_i$ applied to the embeddings sent from v's neighbors and (ii) the output of the functions $g_i$ applied to v's label embeddings. \ The better the output of the functions $\tilde{g}_i$ is able to reconstruct the output of the functions $g_i$, the smaller the value of the distance measure. The gradients are the messages that are propagated back to the neighboring nodes so as to update the corresponding embedding vectors. As illustrated in FIG. 3, for each vertex v, the function f computes a vector representation of the vertex based on the vector representations of v's labels. Here, the label embeddings are first averaged for every label type and the resulting embeddings are concatenated Let $v \in V$, let $i \in \{1, \ldots, k\}$ be a label type, and let $d_i \in \mathbb{N}$ be the size of the embedding for label type i. Moreover, let $h_i(v) = g_i(\{h_l | l \in l_i(v)\})$ and let $\tilde{h}_i(v) = \tilde{g}_i(\{h_l | l \in l_i(N(v))\})$, where $g_i$ and $\tilde{g}_i$ are some differentiable functions that map multisets of $d_i$-dimensional vectors to a single $d_i$-dimensional vector. The vector $h_i(v)$ is referred to as the embedding of label of type i for vortex v and to $\tilde{h}_i(v)$ is referred to as the reconstruction of the embedding of label type i for vertex v since it is computed from the label embeddings of v's neighbors. While the $g_i$ and $\tilde{g}_i$ can be parameterized (typically with a neural network), in many cases they are simple parameter free functions that compute, e.g., the average or maximum of the input.

The first learning procedure is driven by the following objectives for each label type:

$$i \in \{1, \ldots, k\}$$
$$\min \mathcal{L}_i = \min \sum_{v \in V} d_i(\tilde{h}_i(v), h_i(v))$$

where $d_i$ is some measure of distance between $h_i(v)$, the current representation of label type i for vertex v, and its reconstruction $\tilde{h}_i(v)$. Hence, the objective of the approach is to learn the parameters of the functions $g_i$ and $\tilde{g}_i$ (if such parameters exist) and the vector representations of the labels such that the output of $\tilde{g}_i$ applied to the label embeddings of v's neighbors is close to the output of $g_i$ applied to the label embeddings of v. For each vertex v the messages passed to v from its neighbors are the representations of their labels. The messages passed back to v's neighbors are the gradients which are used to update the label embeddings. FIG. 6 illustrates the first part of the unsupervised learning framework for a part of a citation network. A representation is learned both for the article identifiers and the words occurring in the articles. The gradients are computed based on a loss between the reconstruction of the label type embeddings and their current values.

Vector representations of labels might be initialized randomly or with an existing model. For instance, vector representations for words can be initialized using existing word embedding algorithms (Mikolov, T., Sutskever, I., Chen, K., Corrado, G. S., & Dean, J. (2013). Distributed representations of words and phrases and their compositionality. In Advances in neural information processing systems (pp. 3111-3119)) and representations for images with existing CNNs (Krizhevsky, A., Sutskever, I., & Hinton, G. E. (2012). Imagenet classification with deep convolutional neural networks. In Advances in neural information processing systems (pp. 1097-1105) and Frome, A., Corrado, G. S., Shlens, J., Bengio, S., Dean, J., & Mikolov, T. (2013). Devise: A deep visual-semantic embedding model. In Advances in neural information processing systems (pp. 2121-2129)), each of the foregoing publications being incorporated by reference herein. Embeddings initialized by these external methods can then be updated by the application of the proposed machine learning method. It has been empirically demonstrated, however, that random initializations of the vector representations also lead to effective vertex embeddings.

The second step of the proposed learning framework applies a function f to compute the representations of the vertex v from the representations of v's labels:

$$h_v = f(\{h_l | l \in l(v)\})$$

where the label embeddings and the parameters of the functions $g_i$ and $\tilde{g}_i$ (if such parameters exist) remain unchanged. FIG. 3 illustrates the second step of GEMP.

According to a particularly advantageous embodiment, an instance of the GEMP framework, referred to herein as GEMP-B, has been found to be highly effective for several of the typical graph-based learning problems. The instance results from setting $$g_i(H) = \tilde{g}_i(H) = \frac{1}{|H|} \Sigma_{h \in H} h$$

for all label types i and all sets of embedding vectors H. In this case, for any vertex v and any label type i, there exists:

$$\tilde{h}_i(v) = \frac{1}{|l_i(N(v))|} \Sigma_{u \in N(v)} \Sigma_{l \in l_i(u)} h_l. \quad (1)$$

such that $g_i$ computes the average of the label embeddings of the neighboring nodes and is parameter free.

In conjunction with the above functions $g_i$ and $\tilde{g}_i$, the margin-based ranking loss used can be:

$$\mathcal{L}_i = \Sigma_{v \in V} \Sigma_{u \in V \setminus \{v\}} [\gamma + d_i(\tilde{h}_i(v), h_i(v)) - d_i(\tilde{h}_i(u), h_i(u))]_+, \quad (2)$$

where $d_i$ is the Euclidean distance, $[x]_+$ is the positive part of x, and $\gamma > 0$ is a margin hyperparameter. Hence, the objective is to make the distance between $\tilde{h}_i(v)$, the reconstructed embedding of label type i for vertex v, and $h_i(v)$, the current embedding of label type i for vertex v, smaller than the distance between $\tilde{h}_i(v)$ and $h_i(u)$, the embedding of label type i of a vertex u different from v. The minimization problem is solved with gradient decent algorithms and using one node u for every v in each learning iteration.

Finally, a simple instance of the function f is a function that computes, for each label type i, the average embedding and concatenates these average embeddings to form one single vector representation $$h_v = f(\{h_l \mid l \in l(v)\}) = concat\left(\frac{1}{|l_1(v)|}\Sigma_{l \in l_1(v)}h_l, \ldots, \frac{1}{|l_k(v)|}\Sigma_{l \in l_k(v)}h_l\right). \quad (3)$$

FIG. 3 illustrates the working of this particular function f. GEMP-B is based on the formulas (1), (2) and (3). The resulting vector representation of the vertices can now be used for downstream learning problems such as vertex classification, link prediction, and so on. The following analysis of the GEMP framework accomplishes two objectives. First, it states the computational and model complexities of GEMP with respect to properties of the input graphs. Second, it explores the connections to some existing approaches in more detail.

Figure 7:
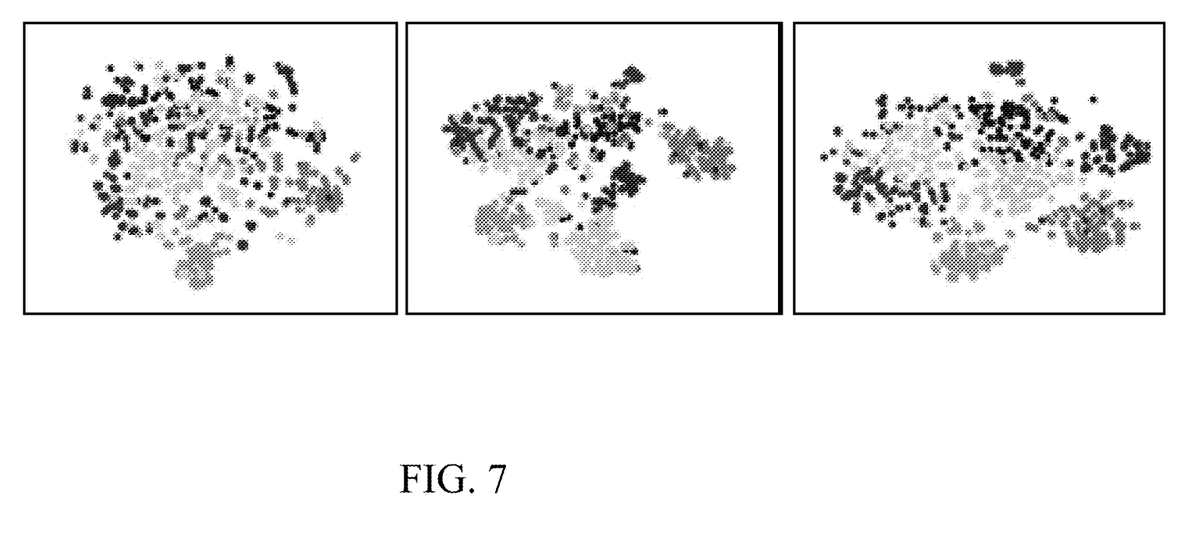
FIG. 7 shows a visualization of the embeddings of 700 nodes (100 per class label) of the Coriolis Ocean database ReAnalysis (CORA) citation network based on only on node identity labels (bottom), based only on word labels (center) and based on the combination of the two (top)

FIG. 7 shows visualizations, best seen in color, of the embeddings of 700 nodes (100 per class label) of the CORA citation network. The two-dimensional vectors were generated by applying t-sne to the 128-dimensional embeddings generated by GEMP-B. The plot visualizes embeddings based only on node identity labels (bottom), embeddings based only on word labels (center), and embeddings based on the combination of the two (top). The Silhouette score, a measure of clustering quality ranging from −1 to 1 (higher is better), is from bottom to top 0:008, 0:107, and 0:158, respectively.

In regard to computational complexity, let G=(V, E) be a graph (either directed or undirected) with k label types L={$L_1$, . . . , $L_k$}. Moreover, let $lab_{max} = \max_{v \in V, i \in \{1, \ldots, k\}} |l_i(V)|$ be the maximum number of labels for any type and any vertex of the input graph, let $deg_{max} = \max_{v \in V} |N(v)|$ be the maximum degree of the input graph, and let τ(n) be the worst-case complexity of computing any of the functions $g_i$ and $\tilde{g}_i$ on n input vectors of size $d_i$. Now, the worst-case complexity of one learning iteration is:

$$O(k|V|\Sigma(lab_{max}deg_{max}))$$

For an input graph without attributes, that is, where the only label type represents node identities, the worst-case complexity of one learning iteration is O(|V|τ($deg_{max}$)). If, in addition, the complexity of the single reconstruction function is linear in the number of input vectors, the complexity is P (|V|$deg_{max}$) and, hence, linear in both the number of nodes and the maximum degree of the input graph.

This is the case for most aggregation functions and, in particular, for the functions $\tilde{g}_i$ and $g_i$ used in GEMP-B, the particular instance of the learning framework defined by the formulas (1), (2), and (3). Furthermore, the average complexity is linear in the average node degree of the input graph.

In general, the worst-case complexity can be limited by not exchanging messages from all neighbors but only a sampled subset of size, at most K. Different sampling scenarios are discussed below. Table 1 below shows a number of parameters and hyperparameters for an input graph G=(V, E) with a single label type representing the vertex identities, that is, a graph without attributes.

TABLE 1

Parameters and hyperparameters for an input graph G = (V, E)

| Method | # parameters | # hyperparameters |
|---|---|---|
| DEEPWALK | 2d|V| | 4 |
| NODE2VEC | 2d|V| | 6 |
| LINE | 2d|V| | 2 |

TABLE 1-continued

Parameters and hyperparameters for an input graph G = (V, E)

| Method | # parameters | # hyperparameters |
|---|---|---|
| PLANETOID | »2d|V| | ≥6 |
| GEMP-B | d|V| | 2 |

In general, the number of parameters and hyperparameters of the learning framework depends on the parameters of the functions $g_i$ and $\tilde{g}_i$, the loss functions, and the number of distinct labels of the input graph.

For graphs without attributes, the only parameters of GEMP-B are the embedding weights and the only hyperparameters are the size of the embedding d and the margin γ. Hence, the number of parameters is d|V| and the number of hyperparameters is two. Table 1 lists the parameter counts for a select set of methods for learning embeddings for graphs without attributes. It has been shown empirically that GEMP-B is highly competitive and often outperforms existing methods such as NODE2VEC and DEEPWALK. These results are somewhat surprising considering that NODE2VEC and DEEPWALK have significantly more parameters to learn and more hyperparameters to calibrate. Thus, GEMP-B provides technological improvements to the computing systems, compared to those using known methods such as NODE2VEC and DEEPWALK, by producing same or better results using less computational resources.

GEMP-B is related to LLE, in which there is a single function $\tilde{g}$ which computes a linear combination of the vertex embeddings. $\tilde{g}$'s weights are learned for each vertex in a separate previous step. Hence, unlike for GEMP-B, $\tilde{g}$ does not compute the unweighted average of the input embeddings. Moreover, LLE is only feasible for graphs where each node has at most a small constant number of neighbors. LLE imposes additional constraints to avoid degenerate solutions to the objective and solves the resulting optimization problem in closed form. This is not feasible for large graphs. Learning the parameters of the functions g and the embeddings in two separate (and possibly alternating) learning procedures, however, is something that could be explored within the GEMP framework. Thus, GEMP provides for significant computational functionality and better results than possible using LLE.

In several applications, the nodes of the graphs are associated with a set of words. For instance, in citation networks, the nodes which represent individual articles can be associated with a bag of words. Every label corresponds to one of the words. FIG. 5 illustrates a part of such a citation network. In this context, GEMP-B's learning of word embeddings is related to the CBOW model. One difference is that for GEMP-B the context of a word is determined by the neighborhood of the vertices it is associated with and it is the embedding of the word that is reconstructed and not its one-hot encoding.

For graphs with several different edge types such as multi-relational graphs, the reconstruction functions $\tilde{g}_i$ can be made dependent on the type of the edge. For instance, one could have, for any vertex v and label type i:

$$\tilde{h}_i(v) = \frac{1}{|l_1(N(v))|}\Sigma_{u \in N(v)}\Sigma_{l \in l_i(u)}(h_l + r_{(u,v)}),$$

where $r_{(u,v)}$ is the vector representation corresponding to the type of the edge (the relation) form vertex u to vertex v, and $h_l(v)$ could be the average embedding of v's labels. In combination with the margin-based ranking loss (2), this is related to embedding models for multi-relational graphs such as TRANSE. In contrast to TRANSE, the reconstruction is here computed by translating and then averaging the label embeddings of several neighboring vertices and not just of one neighbor vertex at a time.

The evaluation of GEMP-B discussed below meets three objectives. First, GEMP-B is compared to the state of the art on node classification problems. Second, the learned representations are visualized. Third, the impact of an upper bound on the number of neighbors that are sending messages is investigated.

GEMP-B is evaluated with regard to the following six commonly used benchmark data sets. BLOGCATALOG is a graph representing the social relationships of the bloggers listed on the BLOGCATALOG website. The class labels represent user interests. PPI is a subgraph of the protein-protein interactions for *Homo Sapiens*. The class labels represent biological states. POS is a co-occurrence network of words appearing in the first million bytes of the Wikipedia dump. The class labels represent the Part-of-Speech (POS) tags. CORA, CITESEER and PUBMED are citation networks where nodes represent documents and their corresponding bag-of-words and links represent citations. The class labels represents the main topic of the evaluation. Whereas BLOGCATALOG, PPI and POS are multi-label classification problems, CORA, CITESEER and PUBMED have exactly one class label per node. Some statistics of these data sets are summarized in Table 2 below.

TABLE 2

Dataset statistics where k is the number of label types

| Dataset | |V| | |E| | # classes | k |
|---|---|---|---|---|
| BLOGCATALOG | 10,312 | 333,983 | 39 | 1 |
| PPI | 3,890 | 76,584 | 50 | 1 |
| POS | 4,777 | 184,812 | 40 | 1 |
| CORA | 2,708 | 5,429 | 7 | 2 |
| CITESEER | 3,327 | 4,732 | 6 | 2 |
| PUBMED | 19,717 | 44,338 | 3 | 2 |

The input to the node classification problem is a graph (with or without node attributes) where a fraction of the nodes is assigned a class label. The output is an assignment of class labels to the test nodes. Using the node classification data sets, the performance of GEMP-B is compared to the state of the art approaches DEEPWALK, LINE, NODE2VEC and PLANETOID, and also to the simple baselines approaches WVRN and MAJORITY. WVRN assigns the class label to a node v that appears most frequently in v's neighborhood. MAJORITY always chooses the most frequent class labels in the training set.

For each label type, the embedding dimension is set to 128 for all methods. This is in line with previous work such as DEEPWALK AND NODE2VEC for some of the data sets under consideration. For GEMP-B, the margin $\gamma$ in (2) is chosen from the set of values [1, 5, 10, 20] on validation data. For all approaches except LINE, the hyperparameter values reported in previous work were used since these values were tuned to the data sets. As LINE has not been applied to the data sets before, its number of samples was set to 20 million and negative samples to 5. This means that LINE is trained on an order of magnitude more examples than all other methods. The evaluation did not simply copy results from previous works but used the authors' codes to run all experiments again. For DEEPWALK, the implementation provided by the authors of NODE2VEC were used (setting p=1.0 and q=1.0). The other hyperparameters values for DEEPWALK reported for NODE2VEC were also used to ensure a fair comparison. Ten runs were performed for each method in each of the experimental set-ups described herein, and the mean and standard deviation of the corresponding evaluation metrics were computed. The same sets of training, validation and test data were used for each method.

All methods were evaluated in the transductive and inductive setting. The transductive setting is the standard setting where all nodes of the input graph are visible during training. In the inductive setting, a certain percentage of the nodes are not part of the graph during unsupervised learning. Instead, these removed nodes are added after the training has concluded and their embeddings are computed from the embeddings of their neighboring nodes The results computed for the nodes not observed during unsupervised training reflect the methods ability to incorporate newly added nodes without retraining the model.

For the graphs without attributes (BLOGCATALOG, PPI and POS), the exact same respective experimental procedures as in the previous works with the respective data sets were used. First, the node embeddings were computed in an unsupervised fashion. Second, a fraction $T_r$ of nodes was sampled uniformly at random and their embeddings and class labels were used as training data for a logistic regression classifier. The embeddings and class labels of the remaining nodes were used as test data. GEMP-B's margin hyperparameter $\gamma$ was chosen by 3-fold cross validation for $T_r$=0.1 once. The resulting margin $\gamma$ was used for the same data set and for all other values of $T_r$. For each, 3-fold cross validation was used to determine the L2 regularization parameter for the logistic regression classifier from the values [0.01, 0.1, 0.5, 1, 5, 10]. This was done for each value of $T_r$ and the F1 macro and F1 micro scores separately. This proved to be important since the L2 regularization had a considerable impact on the performance of the methods.

For the graphs with attributes (CORA, CITESEER and PUBMED), the same experimental procedure as in previous work with these datasets was used. Twenty nodes were sampled uniformly at random for each class as training data, one thousand nodes as test data, and a different one thousand nodes as validation data. In the transductive setting, unsupervised training was performed on the entire graph. In the inductive setting, the one thousand test nodes were removed from the graph before training. For GEMP-B and DEEPWALK, the learned node embeddings for the twenty nodes per class label were fed to a one-vs-rest logistic regression classifier with L2 regularization. The best value was chosen for GEMP-B's margins and the L2 regularizer on the validation set from the values [0.01, 0.1, 0.5, 1, 5, 10]. The same was done for the baselines DW+BOW and FEAT. Since PLANETOID jointly optimizes an unsupervised and supervised loss, the learned models were applied directly to classify the nodes. The authors of PLANEOID did not report the number of learning iterations, so it was ensured the training had converged. This was the case after five thousand, five thousand and twenty thousand training steps for CORA, CITESEER and PUBMED, respectively.

For GEMP-B, ADAM was used to learn the parameters in a mini-batch setting with a learning rate of 0:001. A single learning epoch iterates through all nodes of the input graph and the number of epochs was fixed to two hundred and the mini-batch size to sixty-four. GEMP was implemented with the THEANO wrapper KERAS, and the logistic regression classifier from LIBLINEAR was used. All experiments were run on commodity hardware with 128 GB RAM, a single 2.8 GHz CPU, and a TITANX GPU.

TABLE 3

Multi-label classification results for BLOGCATALOG, POS and PPI in the transductive setting. $T_r$ is the fraction of nodes used during training and $\gamma$ is GEMP-B's margin hyperparameter. The upper and lower part list micro and macro F1 scores, respectively.

| | BLOGCATALOG | | | POS $T_r$ [%] | | | PPI | | |
|---|---|---|---|---|---|---|---|---|---|
| | 10 | 50 | 90 | 10 | 50 | 90 | 10 | 50 | 90 |
| | | $\gamma = 1$ | | | $\gamma = 10$ | | | $\gamma = 5$ | |
| GEMP-B | 35.05 ± 0.41 | 39.44 ± 0.29 | 40.41 ± 1.59 | 46.97 ± 0.36 | 49.52 ± 0.48 | 50.05 ± 2.23 | 17.82 ± 0.77 | 23.30 ± 0.37 | 24.74 ± 1.30 |
| DEEPWALK | 34.48 ± .040 | 38.11 ± 0.43 | 38.34 ± 1.82 | 45.02 ± 1.09 | 49.10 ± 0.52 | 49.33 ± 2.39 | 17.14 ± 0.89 | 23.52 ± 0.65 | 25.02 ± 1.38 |
| NODE2VEC | 34.54 ± 0.49 | 39.31 ± 0.25 | 40.03 ± 1.22 | 44.66 ± 0.92 | 48.73 ± 0.59 | 49.73 ± 2.35 | 17.00 ± 0.81 | 23.31 ± 0.62 | 24.75 ± 2.02 |
| LINE | 34.83 ± 0.39 | 38.99 ± 0.25 | 38.77 ± 1.08 | 45.22 ± 0.86 | 51.64 ± 0.65 | 52.28 ± 1.87 | 16.55 ± 1.50 | 23.01 ± 0.84 | 25.28 ± 1.68 |
| WVRN | 20.50 ± 0.45 | 30.24 ± 0.96 | 33.47 ± 1.50 | 26.07 ± 4.35 | 29.21 ± 2.21 | 33.09 ± 2.27 | 10.99 ± 0.57 | 18.14 ± 0.60 | 21.49 ± 1.19 |
| MAJORITY | 16.51 ± 0.53 | 16.88 ± 0.35 | 16.53 ± 0.74 | 40.40 ± 0.62 | 40.47 ± 0.51 | 40.10 ± 2.57 | 6.15 ± 0.40 | 5.94 ± 0.66 | 5.66 ± 0.92 |
| GEMP-B | 19.08 ± 0.78 | 25.11 ± 0.43 | 25.97 ± 1.25 | 8.85 ± 0.33 | 10.45 ± 0.69 | 12.17 ± 1.19 | 13.80 ± 0.67 | 18.96 ± 0.43 | 20.36 ± 1.42 |
| DEEPWALK | 18.16 ± 0.44 | 22.65 ± 0.49 | 22.86 ± 1.03 | 8.20 ± 0.27 | 10.84 ± 0.62 | 12.23 ± 1.38 | 13.01 ± 0.90 | 18.73 ± 0.59 | 20.01 ± 1.82 |
| NODE2VEC | 19.08 ± 0.52 | 23.97 ± 0.58 | 24.82 ± 1.00 | 8.32 ± 0.36 | 11.07 ± 0.60 | 12.11 ± 1.93 | 13.32 ± 0.49 | 18.57 ± 0.49 | 19.66 ± 2.34 |
| LINE | 18.13 ± 0.33 | 22.56 ± 0.49 | 23.00 ± 0.92 | 8.49 ± 0.41 | 12.43 ± 0.81 | 12.40 ± 1.18 | 12.79 ± 0.48 | 18.06 ± 0.81 | 20.59 ± 1.59 |
| WVRN | 10.86 ± 0.87 | 17.46 ± 0.74 | 20.10 ± 0.98 | 4.14 ± 0.54 | 4.42 ± 0.35 | 1.41 ± 0.53 | 8.60 ± 0.57 | 14.65 ± 0.74 | 17.50 ± 1.42 |
| MAJORITY | 2.51 ± 0.09 | 2.57 ± 0.08 | 2.53 ± 0.31 | 3.38 ± 0.13 | 3.36 ± 0.14 | 3.36 ± 0.44 | 1.58 ± 0.25 | 1.51 ± 0.27 | 1.44 ± 0.35 |

TABLE 4

Multi-label classification results for BLOGCATALOG, POS and PPI in the inductive setting for $T_r = 0.1$. $\gamma$ is GEMP-B's margin hyperparameter. The upper and lower part of the table list micro and macro F1 scores, respectively.

| | BLOGCATALOG | | POS | | PPI | |
|---|---|---|---|---|---|---|
| | | | Removed Nodes [%] | | | |
| | 20 | 40 | 20 | 40 | 20 | 40 |
| GEMP-B | $\gamma = 10$ | $\gamma = 5$ | $\gamma = 10$ | $\gamma = 10$ | $\gamma = 10$ | $\gamma = 10$ |
| | 29.22 ± 0.95 | 27.30 ± 1.33 | 43.23 ± 1.44 | 42.12 ± 0.78 | 16.63 ± 0.98 | 14.87 ± 1.04 |
| DEEPWALK-I | 27.84 ± 1.37 | 27.14 ± 0.99 | 40.92 ± 1.11 | 41.02 ± 0.70 | 15.55 ± 1.06 | 13.99 ± 1.18 |
| LINE-I | 19.15 ± 1.30 | 19.96 ± 2.44 | 40.34 ± 1.72 | 40.08 ± 1.64 | 14.89 ± 1.16 | 13.55 ± 0.90 |
| WVRN | 19.36 ± 0.59 | 19.07 ± 1.53 | 23.35 ± 0.66 | 27.91 ± 0.53 | 8.83 ± 0.91 | 9.41 ± 0.94 |
| MAJORITY | 16.84 ± 0.686 | 16.81 ± 0.55 | 40.43 ± 0.86 | 40.59 ± 0.55 | 6.09 ± 0.40 | 6.39 ± 0.61 |
| GEMP-B | $\gamma = 10$ | $\gamma = 5$ | $\gamma = 10$ | $\gamma = 10$ | $\gamma = 10$ | $\gamma = 10$ |
| | 12.12 ± 0.75 | 11.24 ± 0.89 | 5.47 ± 0.80 | 5.16 ± 0.49 | 11.55 ± 0.90 | 10.38 ± 0.90 |
| DEEPWALK-I | 11.96 ± 0.88 | 10.91 ± 0.95 | 4.54 ± 0.32 | 4.46 ± 0.57 | 10.52 ± 0.56 | 9.69 ± 1.14 |
| LINE-I | 6.64 ± 0.49 | 6.54 ± 1.87 | 4.67 ± 0.46 | 4.24 ± 0.52 | 9.86 ± 1.07 | 9.15 ± 0.74 |
| WVRN | 9.45 ± 0.65 | 9.18 ± 0.62 | 3.74 ± 0.64 | 3.87 ± 0.44 | 6.90 ± 1.02 | 6.81 ± 0.89 |
| MAJORITY | 2.50 ± 0.18 | 2.59 ± 0.19 | 3.35 ± 0.24 | 3.27 ± 0.15 | 1.54 ± 0.31 | 1.55 ± 0.26 |

The results for BLOGCATALOG, POS and PPI in the transductive setting are listed in Table 3. It is observed that GEMP-B tends to have better F1 scores than DEEPWALK, LINE and NODE2VEC, with the additional aforementioned advantage of fewer parameters and hyperparameters to tune. Even though the hyperparameter values reported in NODE2VEC were used, no significant differences to DEEPWALK were observed. This is contrary to earlier findings, which is most possibly due to validating the L2 regularization of the logistic regression classifier being crucial and not having been performed in the earlier work. The F1 scores of GEMP-B, DEEPWALK, LINE and NODE2VEC are significantly higher than those of the simple baselines WVRN and MAJORITY.

The results for the same data sets in the inductive setting are listed in Table 4 for different percentages of nodes removed before unsupervised training. GEMP reconstructs label embeddings from the embeddings of labels of neighboring nodes. Hence, with GEMP-B, it is possible to directly use the concatenation of the reconstructed embedding $\tilde{h}_i(v)$ as the node embedding for each of the nodes v that were not part of the graph during training. Since the F1 scores of NODE2VEC in the transductive setting were not significantly different to that of DEEPWALK, NODE2VEC was not included in the experiments. For DEEPWALK and LINE, embeddings of nodes removed before unsupervised training were computed by averaging the embeddings of neighboring nodes; this is indicated by the suffix I. GEMP-B outperforms all these methods in the inductive setting.

The results for the data sets CORA, CITESEER and PUBMED are listed in Table 5. Since these data sets have bag of words associated with nodes, the baseline method DW+BOW is included. DW+BOW concatenates the embedding of a node learned by DEEPWALK with a vector that encodes the bag of words of the node. PLANETOID-T and PLANETOID-I are the transductive and inductive formulation of PLANETOID. Contrary to other methods, GEMP-B's F1 scores on the transductive and inductive setting are very similar, demonstrating its suitability for the inductive setting. DEEPWALK cannot make use of the word labels, but is included in the evaluation to investigate to what extent the word labels improve the performance of the other methods. The baseline FEAT trains a logistic regression classifier on the binary vectors encoding the bag of words of each node. GEMP-B significantly outperforms all existing approaches in both the transductive and inductive setting on all three data sets. Both PLANETOID-T and DW+BOW do not take full advantage of the information given by the bag of words, since the encoding of the bag of words is only exposed to the respective models for nodes with class labels and, therefore, only for a small fraction of nodes in the graph. This could also explain PLANETOID-T's high standard deviation since some nodes might be associated with words that occur in the test data, but which might not have been encountered during training. This would lead to misclassifications of these nodes. GEMP-B jointly learns embeddings of several attributes in an unsupervised manner and combines these into a node embedding.

TABLE 5

Classification accuracy for CORA, CITESEER and PUBMED. The upper and lower part of the table list the results for the transductive and inductive setting, respectively.

| Method | CORA | CITESEER | PUBMED |
|---|---|---|---|
| GEMP-B | $\gamma = 20$ | $\gamma = 10$ | $\gamma = 1$ |
|  | 78.05 ± 1.49 | 71.01 ± 1.35 | 79.56 ± 2.10 |
| DW + BOW | 76.15 ± 2.06 | 61.87 ± 2.30 | 77.82 ± 2.19 |
| PLANETOID-T | 71.90 ± 5.33 | 58.58 ± 6.35 | 74.49 ± 4.95 |
| DEEPWALK | 71.11 ± 2.70 | 47.60 ± 2.34 | 73.49 ± 3.00 |
| GEMP-B | $\gamma = 5$ | $\gamma = 5$ | $\gamma = 1$ |
|  | 73.09 ± 1.75 | 68.61 ± 1.69 | 79.94 ± 2.30 |
| DW-I + BOW | 68.35 ± 1.70 | 59.47 ± 2.48 | 74.87 ± 1.23 |
| PLANETOID-I | 64.80 ± 3.70 | 61.97 ± 3.82 | 75.73 ± 4.21 |
| FEAT | 58.63 ± 0.68 | 58.07 ± 1.72 | 70.49 ± 2.89 |

FIG. 7 depicts a visualization of the learned embeddings for the CORA citation network. Both qualitatively and quantitatively, the visualization demonstrates GEMP-B's ability to learn and combine embeddings of several label types.

Up until now, the direction of the edges have not been taken into account, that is, all graphs have been treated as undirected. Citation networks, however, are intrinsically directed. Table 6 shows the performance of GEMP-B and DEEPWALK when the edge directions are considered. For GEMP, this means label representations are only sent along the directed edges. For DEEPWALK, this means that the generated random walks are directed walks. While a significant performance deterioration for DEEPWALK was observed, the accuracy of GEMP-B does not change significantly. This demonstrates that GEMP is also applicable when edge directions are taken into account and, in fact, is far more accurate despite utilizing fewer resources and providing a higher computing performance than DEEPWALK and the other methods. As already mentioned above, GEMP does utilizes less parameters and/or hyperparameters than the other methods, which results in utilization of fewer computational resources and memory, and provides quicker and more accurate computations of personalizations. Moreover, new nodes can be added at greatly reduced computational cost by using the label latent representations of neighboring nodes.

Figure 8:
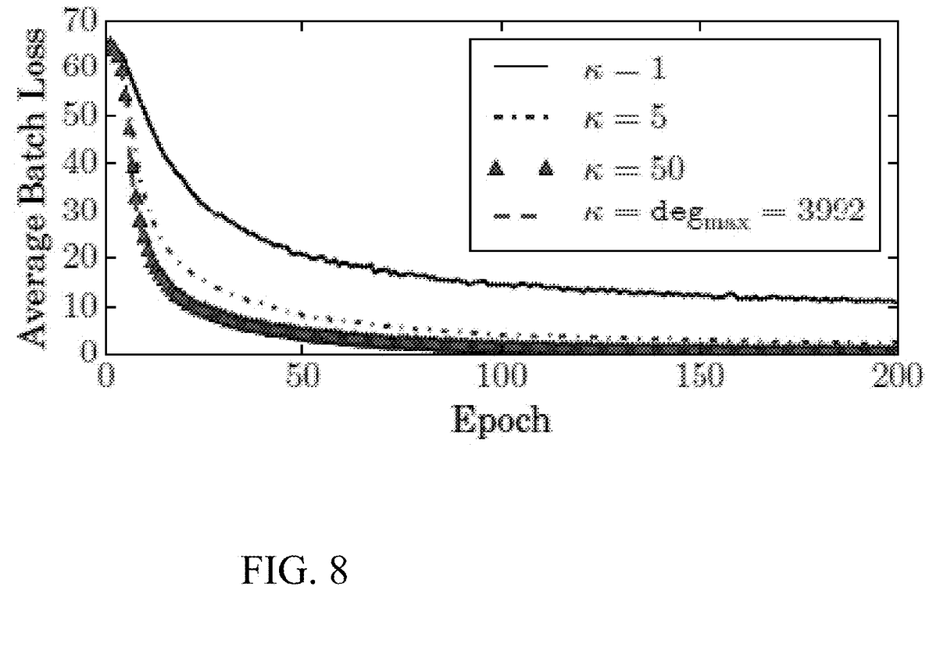
FIG. 8 is a graph showing average batch loss versus a number of epochs for different values of the parameter κ which is the upper bound on the number of neighbors randomly chosen to send messages.

For densely connected graphs with a high average degree, it is beneficial to limit the number of neighbors that send label representations in each learning step. This can be accomplished by sampling a subset of at most size $\kappa$ from the set of all neighbors and to send messages only from the sampled nodes. The impact of this strategy was evaluated by varying the parameter $\kappa$. FIG. 8 plots the average batch loss vs. the number of learning iterations for the Product-Catelog data set and for different values of $\kappa$. $\kappa$ is the upper bound on the number of neighbors randomly chosen to send messages. Training time per epoch is 20 seconds for $\kappa=\deg_{max}=3992$ and less than 1 second for the other values of $\kappa$. The loss is significantly higher for smaller values of $\kappa$ but for $\kappa=50$ the average loss is almost identical to the case where all neighbors send messages. The training time per epoch is reduced from about 20 seconds for all neighbors to less than 1 second for $\kappa=50$. The sampling strategy, therefore, can be used to increase efficiency while keeping the loss of model quality at a minimum.

TABLE 6

Classification accuracy for the CORA, CITESEER and PUBMED data sets. The results are for the transductive setting where the directionality of the edges is taken into account.

| Method | CORA | CITESEER | PUBMED |
|---|---|---|---|
| GEMP-B | $\gamma = 20$ | $\gamma = 5$ | $\gamma = 1$ |
|  | 77.31 ± 1.43 | 70.21 ± 1.17 | 78.77 ± 2.06 |
| DEEPWALK | 14.82 ± 2.15 | 15.79 ± 3.58 | 32.82 ± 2.12 |

Thus, GEMP is an unsupervised machine learning framework for graph-structured data. It learns label and node representations by exchanging messages between nodes. It supports arbitrary label types such as node identities, text, movie genres, and generalizes several existing approaches. It has been demonstrated that GEMP-B, a simple instance of GEMP, is competitive with and often outperforms state of the art methods while having fewer parameters and/or hyperparameters. In further embodiments, GEMP can be combined with multitask learning, that is, learning the embeddings of labels and nodes guided by both an unsupervised and supervised loss; a variant of GEMP that incorporates image data; the integration of GEMP with an existing distributed graph processing framework; and the application of the GEMP framework to multi-relational graphs.

A first particular application of GEMP according to an embodiment of the invention is in a digital health personalization system in which:

The Data Collection Component: The nodes would represent patients and consequently it would collect test results, medical imaging, technical reports, etc. of the patients by connecting to this information through health networks or by accessing databases containing such information, or by being provided with this information from the patients or health professionals.

The Node Addition Component: It creates edges with existing nodes, e.g., upon a determination that two patients (the existing and the new one) share all or a subset of symptoms.

The Classifier/Regressor Component can be trained for different purposes. Disease detection is a relatively straightforward classification problem.

The Personalization Component, based on the output of the Classifier/Regressor component, maps these outputs to actions to mitigate or alleviate their effects. For instance, it might take the disease detected by the Classifier/Regressor component and output a treatment that has been found effective in the past for such disease. This Component is trained with medical records of actions that have mitigated symptoms (described by X-ray, blood test . . . ) presented in patients in the past.

A second particular application of GEMP according to an embodiment of the invention is in a computing system for public safety in which:

The Data Collection Component: The nodes can represent, e.g., geographical spots (defined by a range of geocoordinates). This component would collect crime statistics of that area, but also information such as the money invested by the municipality in schools or police patrols, as well as binary features indicating whether there exists a fire or a police station, to name, but a few examples of information that the model might collect. This type of information is generally publicly available and/or accessible via network or database.

The Node Addition Component: There may exist a link connecting two geographical spots if they are geographically close (e.g., within a certain distance d) or based on prior experience. Once a new node and its corresponding links to existing nodes in the graphs are added, then the Data Collection Component would collect crime statistics of this new area.

The Classifier/Regressor Component: For an example, an application may be interested in predicting, for each geographical spot, the cost the crimes will cause to the state for the upcoming year. In general, any application where the output is potentially correlated with the crime information is plausible. For instance, the intention of vote in the elections may be in high correlation with the crime statistics.

The Personalization Component: The government of a state can deploy some prevention and protection measures (for example, by increasing the presence of police patrols in certain areas, the access to mental health services or the investment in education) in those areas for which the Classifier/Regressor Component has predicted a high cost derived from public safety incidents. Other actions can include issuing automated alerts to public officials or changing the displays of electronic signs.

Advantages and advancements achieved by embodiments of the present invention include:

1. Graph-based machine learning algorithm that operates by passing messages to learn a latent node representation;
2. Latent representations of nodes are learned based on latent representations of labels, and these labels may be of varying types. Each label type can be treated by a convenient dedicated network;
3. Latent node representations are used to personalize products and services; and/or
4. Provides a completely unsupervised method (class labels are not needed to learn the representations), and is therefore agnostic to the application.

Latent representations perform better in a range of applications compared to raw representations (see U.S. Pat. Nos. 9,384,571 and 8,538,169 and U.S. Patent Publication No. 2014/0244293).

According to an embodiment, the method comprises the steps of:

1. Data collection and preprocessing and addition of nodes and labels to the graph representations;
2. Learning node representations via message passing;
3. Using the node representations to train a classifier/regressor for a certain personalization; and
4. Take actions based on the particular personalization decided on.

In sum, the method is highly efficient and can be applied to very large graphs. Moreover, it has been shown that this framework has a very high accuracy in several problem domains. The approach has been extensively tested on a number of graph-based machine learning problems. The machine learning component does not need to be retrained to generate a vector representation for a newly added node. An average representation (computed as the average of the neighboring node representations) can be computed in real-time and without losing much accuracy. This way the system does not have to be retrained.

Embodiments of the present invention have particular application in:

1. Public safety: nodes represent users and their attributes; edges are relationships to other users entities; goal is to predict whether a user is a security threat;
2. Digital health: nodes represent patients and their attributes; edges represent interaction with hospitals, doctors, similarity of symptoms with other patients; goal is to personalize the treatment of patients, assist the doctors with a diagnosis; and/or
3. Online advertisement: nodes represent users and their attributes; edges represent similarity in online behavior (e.g. HTTP requests); goal is to serve targeted ads to the users.

The proposed method and system is highly efficient. It can compute node representations within milliseconds and is, at the same time, highly accurate. For large graphs which are typically generated in most embodiments, the message passing approach is especially suitable for the parallel/distributed setting, as well as for similar, graph-based personalization systems.

While the invention has been illustrated and described in detail in the drawings and foregoing description, such illustration and description are to be considered illustrative or exemplary and not restrictive. It will be understood that changes and modifications may be made by those of ordinary skill within the scope of the following claims. In particular, the present invention covers further embodiments with any combination of features from different embodiments described above and below. Additionally, statements made herein characterizing the invention refer to an embodiment of the invention and not necessarily all embodiments.

The terms used in the claims should be construed to have the broadest reasonable interpretation consistent with the foregoing description. For example, the use of the article "a" or "the" in introducing an element should not be interpreted as being exclusive of a plurality of elements. Likewise, the recitation of "or" should be interpreted as being inclusive, such that the recitation of "A or B" is not exclusive of "A and B," unless it is clear from the context or the foregoing description that only one of A and B is intended. Further, the recitation of "at least one of A, B and C" should be interpreted as one or more of a group of elements consisting of A, B and C, and should not be interpreted as requiring at least one of each of the listed elements A, B and C, regardless of whether A, B and C are related as categories or otherwise. Moreover, the recitation of "A, B and/or C" or "at least one of A, B or C" should be interpreted as including any singular entity from the listed elements, e.g., A, any subset from the listed elements, e.g., A and B, or the entire list of elements A, B and C.

What is claimed is:

1. A method for learning latent representations of nodes in a personalization system using a graph-based machine learning framework, the method comprising:

generating a graph representation containing the nodes based on input data;
associating the nodes with labels;
learning node vector representations by combining label latent representations from a vertex and neighboring nodes so as to reconstruct the label latent representation of the vertex and updating the label latent representations of the neighboring nodes using gradients resulting from application of a reconstruction loss, wherein the node vector representations are learned using message passing, wherein the label latent representations of the neighboring nodes are sent to the vertex from the neighboring nodes and are combined with a current label latent representation of the vertex so as to reconstruct the label latent representation of the vertex, and wherein the gradients are sent from the vertex to the neighboring nodes;

training a classifier/regressor using the node vector representations and mapping the node vector representations to personalizations; and initiating actions associated with the personalizations.

2. The method according to claim 1, wherein the steps of combining and updating in the learning of the node vector representations are repeated until a convergence threshold is reached.

3. The method according to claim 1, further comprising computing a new node vector representation for a new node being added to the graph representation using label latent representations of neighboring nodes.

4. The method according to claim 1, wherein the nodes represent patients, the graph representation is of a patient-disease network, the labels include symptoms of the patients, the personalizations include diseases detected by the classifier/regressor and the actions include generating a treatment plan based on the detected diseases.

5. The method according to claim 4, further comprising computing a new node vector representation for a new patient added to the patient-disease network and creating edges with existing nodes that share at least some of the same symptoms as the new patient.

6. The method according to claim 1, wherein the nodes represent geographical locations, the graph representation provides the geographical locations that are close to each other as neighboring nodes, the labels include public safety information of the geographical locations, the personalizations include a prediction of one or more of the geographical locations that has a higher cost derived from public safety incidents and the actions include sending an electronic alert to safety officials so that additional prevention and protection measures are deployed in the one or more of the geographical locations.

7. The method according to claim 1, wherein the nodes represent online consumers, the graph representation provides the online consumers having similar online behavior as neighboring nodes, the labels include attributes of the online consumers, the personalizations include a product offered for sale online and the actions include generating an online advertisement for the product that is directed to a computing device of a respective one of the online consumers for which the classifier/regressor determined the personalization.

8. The method according to claim 1, wherein the gradients are computed based on a loss between the reconstructed label latent representation of the vertex and the current label latent representation of the vertex.

9. The method according to claim 1, wherein label latent representations of non-neighboring nodes are not used to reconstruct the label latent representation of the vertex, and wherein the gradients are not used for updating the label latent representations of the non-neighboring nodes.

10. The method according to claim 1, wherein the gradients are derived from distances between outputs of functions applied to the label latent representations of the neighboring nodes and outputs of functions applied to the label latent representation of the vertex such that the gradients move the label latent representations in a Euclidean space of the graph representation until the reconstruction loss reaches a minimum.

11. A personalization system which learns latent representations of nodes using a graph-based machine learning framework, the personalization system consisting of one or more computer processors which, alone or in combination, provide for the execution of the following steps:

generating a graph representation containing the nodes based on input data;

associating the nodes with labels;

learning node vector representations by combining label latent representations from a vertex and neighboring nodes so as to reconstruct the label latent representation of the vertex and updating the label latent representations of the neighboring nodes using gradients resulting from application of a reconstruction loss, wherein the node vector representations are learned using message passing, wherein the label latent representations of the neighboring nodes are sent to the vertex from the neighboring nodes and are combined with a current label latent representation of the vertex so as to reconstruct the label latent representation of the vertex, and wherein the gradients are sent from the vertex to the neighboring nodes;

training a classifier/regressor using the node vector representations and mapping the node vector representations to personalizations; and initiating actions associated with the personalizations.

12. The personalization system according to claim 11, wherein the steps of combining and updating in the learning of the node vector representations are repeated until a convergence threshold is reached.

13. The personalization system according to claim 11, wherein the one or more computer processors, alone or in combination, are further configured to provide for the execution of the step of computing a new node vector representation for a new node being added to the graph representation using label latent representations of neighboring nodes.

14. The personalization system according to claim 11, wherein the nodes represent patients, the graph representation is of a patient-disease network, the labels include symptoms of the patients, the personalizations include diseases detected by the classifier/regressor and the actions include generating a treatment plan based on the detected diseases, and wherein the one or more computer processors, alone or in combination, are further configured to provide for the execution of the step of computing a new node vector representation for a new patient added to the patient-disease network and creating edges with existing nodes that share at least some of the same symptoms as the new patient.

15. The personalization system according to claim 11, wherein the nodes represent geographical locations, the graph representation provides the geographical locations that are close to each other as neighboring nodes, the labels include public safety information of the geographical locations, the personalizations include a prediction of one or more of the geographical locations that has a higher cost derived from public safety incidents and the actions include generating an electronic alert to safety officials so that additional prevention and protection measures are deployed in the one or more of the geographical locations.

16. The personalization system according to claim 11, wherein the nodes represent online consumers, the graph representation provides the online consumers having similar online behavior as neighboring nodes, the labels include attributes of the online consumers, the personalizations include a product offered for sale online and the actions include generating an online advertisement for the product that is directed to a computing device of a respective one of the online consumers for which the classifier/regressor determined the personalization.

17. The personalization system according to claim 11, wherein the gradients are computed based on a loss between the reconstructed label latent representation of the vertex and the current label latent representation of the vertex.

* * * * *